(12) United States Patent
Stopek et al.

(10) Patent No.: US 8,974,776 B2
(45) Date of Patent: Mar. 10, 2015

(54) BIODEGRADABLE PEPTIDE RELEASING POLYMERS

(75) Inventors: Joshua B. Stopek, Yalesville, CT (US); Brian Cuevas, Cumming, GA (US)

(73) Assignee: Covidien LP, Mansfield, MA (US)

( * ) Notice: Subject to any disclaimer, the term of this patent is extended or adjusted under 35 U.S.C. 154(b) by 1232 days.

(21) Appl. No.: 12/599,772

(22) PCT Filed: May 14, 2008

(86) PCT No.: PCT/US2008/063571
§ 371 (c)(1),
(2), (4) Date: Jul. 22, 2010

(87) PCT Pub. No.: WO2008/141326
PCT Pub. Date: Nov. 20, 2008

(65) Prior Publication Data
US 2010/0297066 A1  Nov. 25, 2010

Related U.S. Application Data

(60) Provisional application No. 60/930,110, filed on May 14, 2007.

(51) Int. Cl.
| | | |
|---|---|---|
| *A61K 45/00* | (2006.01) | |
| *A61K 9/00* | (2006.01) | |
| *A61K 47/48* | (2006.01) | |
| *A61L 24/00* | (2006.01) | |
| *A61L 24/06* | (2006.01) | |
| *A61L 27/18* | (2006.01) | |
| *A61L 27/54* | (2006.01) | |
| *A61L 27/58* | (2006.01) | |

(52) U.S. Cl.
CPC ............ *A61K 9/0024* (2013.01); *A61K 47/482* (2013.01); *A61K 47/48215* (2013.01); *A61L 24/0015* (2013.01); *A61L 24/0042* (2013.01); *A61L 24/06* (2013.01); *A61L 27/18* (2013.01); *A61L 27/54* (2013.01); *A61L 27/58* (2013.01); *A61L 2300/25* (2013.01); *A61L 2300/252* (2013.01); *A61L 2300/604* (2013.01)
USPC ......................................................... 424/85.2

(58) Field of Classification Search
USPC ......................................................... 424/85.2
See application file for complete search history.

(56) References Cited

U.S. PATENT DOCUMENTS

| | | | |
|---|---|---|---|
| 5,510,121 A | 4/1996 | Rhee et al. | |
| 7,202,325 B2 | 4/2007 | Pacetti et al. | |
| 2002/0041898 A1* | 4/2002 | Unger et al. | .......... 424/486 |
| 2004/0170685 A1 | 9/2004 | Carpenter et al. | |

FOREIGN PATENT DOCUMENTS

| | | |
|---|---|---|
| EP | 1044693 A1 | 10/2000 |
| WO | WO 92/22599 A1 | 12/1992 |
| WO | WO 99/59548 A1 | 11/1999 |
| WO | WO 00/43435 A1 | 7/2000 |
| WO | WO 2005/027957 A1 | 3/2005 |
| WO | WO 2005/099768 A2 | 10/2005 |
| WO | WO 2005/115489 A2 | 12/2005 |

OTHER PUBLICATIONS

European Search Report for EP 08755429.1-1216 date of completion is Jul. 16, 2012 (20 pages).
International Search Report for PCT/US08/63571 date of completion is Aug. 10, 2008 (2 pages).
Tom et al. Bradykinin potentiation by ACE inhibitors: a matter of metabolism. British Journal of Pharmacology 2002, vol. 137, p. 276-284; abstract.

* cited by examiner

*Primary Examiner* — Benjamin Packard

(57) ABSTRACT

Novel biodegradable compositions are disclosed. The biodegradable compositions include at least one hydroxyl-terminated component and at least one bioactive peptide in a linear chain. The compositions may be utilized as medical devices including drug delivery devices, tissue adhesives and/or sealants.

24 Claims, No Drawings

BIODEGRADABLE PEPTIDE RELEASING POLYMERS

CROSS-REFERENCE TO RELATED APPLICATIONS

This application is a National Stage Application of PCT/US2008/063571 under 35 USC §371(a), which claims priority of U.S. Provisional Patent Application Ser. No. 60/930,110 filed May 14, 2007, the disclosures of each of the above-identified applications are hereby incorporated by reference in their entirety.

BACKGROUND

1. Technical Field

The present disclosure relates to biodegradable peptide releasing polymers and their use in the formation of compositions, such as drug delivery devices, adhesives or tissue sealants.

2. Background of Related Art

A number of synthetic polymers have been described for use in making sutures and other bioresorbable medical devices. Effective synthetic absorbable sutures, as well as other medical devices such as haemostatic aids, intraosseous implants, slow-release drug delivery systems, and tissue regeneration devices including nerve channels, speint ducts, vascular graphs, Fallopian tube ducts and the like, must satisfy a number of biological, physical and chemical requirements. Among these requirements are that the material be bioresorbable, non-carcinogenic, non-antigenic, and non-toxic.

Synthetic polymers have also been used as adhesives or sealants to replace or augment the use of sutures in wound closure. Reasons for the increased interest in the use of such adhesives and/or sealants include: (1) the potential speed with which repair might be accomplished; (2) the ability of a bonding substance to effect complete closure, thus preventing seepage of fluids; and (3) the possibility of forming a bond without excessive deformation of tissue.

For surgical adhesives to be accepted by surgeons, they should exhibit high initial tack and an ability to bond rapidly to living tissue; the strength of the bond should be sufficiently high to cause tissue failure before bond failure; the adhesive should form a bridge, typically a permeable flexible bridge; and the adhesive bridge and/or its metabolic products should not cause local histotoxic or carcinogenic effects.

Several materials useful as tissue adhesives or tissue sealants are currently available. One type of adhesive that is currently available is a cyanoacrylate adhesive. However, cyanoacrylate adhesives can have a high flexural modulus which can limit their usefulness. Another type of tissue sealant that is currently available utilizes components derived from bovine and/or human sources. For example, fibrin sealants are available. However, as with any natural material, variability in the material can be observed.

It would be desirable to provide a fully synthetic material suitable for use as a drug delivery device, biological adhesive, and/or sealant.

SUMMARY

The present disclosure provides biodegradable compositions capable of releasing bioactive peptides in vivo. The biodegradable compositions include, in embodiments, ester oligomers and polymers. These biodegradable compositions degrade in vivo, whereby bioactive peptides within the polymer chain may be released as the polymer degrades. The compositions of the present disclosure may be utilized, in embodiments, as drug delivery devices, tissue adhesives and/or sealants.

In embodiments, a biodegradable composition in accordance with the present disclosure may include at least one hydroxyl-terminated component and at least one bioactive peptide, wherein the biodegradable composition comprises a linear chain and degradation of the at least one hydroxyl-terminated component releases the bioactive peptide in vivo.

The present disclosure also provides methods which may include polymerizing at least one cyclic monomer in the presence of a hydroxy functional peptide to form a copolymer, and recovering the resulting copolymer.

DETAILED DESCRIPTION

The present disclosure relates to novel biodegradable compositions. The polymers are biocompatible, non-immunogenic and biodegradable. In embodiments, the biodegradable compositions may be utilized as drug delivery devices, tissue adhesives, or sealants. Drug delivery devices will degrade in vivo releasing bioactive agents, such as peptides. Adhesives and/or sealants may be employed to adhere tissue edges, seal air/fluid leaks in tissues, adhere medical devices, i.e. implants, to tissue, and for tissue augmentation such as sealing or filling voids or defects in tissue. The compositions can be applied to living tissue and/or flesh of animals, including humans.

The biodegradable compositions of the present disclosure may include ester derived oligomers and polymers. In embodiments, the biodegradable compositions may be generated by reacting a hydroxyl-terminated component with a peptide to form a linear chain including both the hydroxyl-terminated component and the peptide.

Suitable hydroxyl-terminated components include, for example, hydroxyl-terminated polyesters, and/or poly(ether-esters) such as poly(ether-ester) blocks. Suitable polyesters which may be utilized are within the purview of those skilled in the art and include, for example, polymers and copolymers of trimethylene carbonate, ε-caprolactone, p-dioxanone, glycolide, lactide, 1,5-dioxepan-2-one, polybutylene adipate, polyethylene adipate, and polyethylene terephthalate. Suitable poly(ether-ester) blocks are within the purview of those skilled in the art and include, but are not limited to, combinations including copolymers of polyethers such as polyethylene glycol, polypropylene glycol, polybutylene glycol, polytetramethylene glycol and/or polyhexamethylene glycol with the polyesters described above. Specific examples of suitable poly(ether-ester) blocks include, for example, polyethylene glycol-polycaprolactone, polyethylene glycol-polylactide, polyethylene glycol-polyglycolide, polyethylene glycol-lactide-glycolide, polyethylene glycol-lactide-caprolactone, polyethylene glycol-trimethylene carbonate, polyethylene glycol-trimethylene carbonate-lactide, polyethylene glycol-trimethylene carbonate-glycolide, polyethylene glycol-trimethylene carbonate-caprolactone, polyethylene glycol-glycolide-caprolactone, and the like. Additional examples of poly(ether-ester) blocks are disclosed in U.S. Pat. No. 5,578,662 and U.S. Patent Application No. 2003/0135238, the entire disclosures of each of which are incorporated by reference herein.

In embodiments, the hydroxyl-terminated precursor components can be glycolide, lactide, glycolide-polyethylene glycol-caprolactone copolymers, aliphatic oligoesters, polymers and copolymers thereof, and the like.

The hydroxyl-terminated components may be reacted with a peptide, in embodiments a peptide having at least one primary or secondary amino group. As used herein, "peptide" includes amino acids, peptides, oligopeptides, polypeptides, and proteins. A peptide, as used herein, generally includes two or more amino acids connected to each other. An oligopeptide possesses from about 10 to about 50 amino acids connected to one another. A polypeptide possesses a chain of greater than about 50 amino acids connected to one another. A protein is a large macromolecule having a molecular weight of greater than about 2,000 and may be composed of one or more polypeptide chains.

Suitable peptides for conjugation to the hydroxyl-teitninated components to form the compositions of the present disclosure may have biological activity and may be referred to herein, in embodiments, as bioactive peptides. Thus, upon degradation of the linear biodegradable composition in vivo, especially at the location of the hydroxyl-terminated components, the bioactive peptides may be released whereupon they may exert a desired biological effect.

Once chosen for inclusion in a composition of the present disclosure, the bioactive peptide may be prepared or obtained from commercial suppliers for incorporation into a composition of the present disclosure. The bioactive peptide may be prepared using standard synthetic techniques, recombinant technology, or extraction from natural sources.

Synthetic production of peptides, oligopeptides, polypeptides and/or proteins may employ techniques of standard solid phase peptide synthesis within the purview of those skilled in the art. Synthesis may be sequentially carried out by incorporating the desired amino acid residues one at a time onto a growing peptide chain according to general principles of solid phase synthesis as described, for example, by Merrifield (1963) J. Amer. Chem. Soc. 85:2149-2154. A common feature of the chemical syntheses of peptides, polypeptides and proteins is the protection of reactive side chain groups of the various amino acid moieties with suitable protecting groups that will prevent a chemical reaction from occurring at that site until the protecting group is ultimately removed. In some cases, it may be desirable to protect the alpha-amino group on an amino acid while that entity reacts at the carboxyl group, followed by the selective removal of the alpha-amino protecting group to allow a subsequent reaction to take place at that site. Examples of suitable alpha-amino and side chain protecting groups are within the purview of those skilled in the art.

In other embodiments, peptides, oligopeptides, polypeptides and/or proteins may be prepared by employing recombinant technology utilizing techniques within the purview of those skilled in the art. In embodiments, recombinant techniques that may be utilized include constructing DNA encoding the desired amino acid sequence, cloning the DNA into an expression vector, transfoll ing a host cell such as bacterial, yeast, or mammalian cell, and expressing the DNA to produce the desired peptide, oligopeptide, polypeptide or protein.

Additionally, peptides, oligopeptides, polypeptides and/or proteins can be obtained from natural sources such as a human or other animal, and may be extracted from either a living organism or from a cadaver. The peptides, oligopeptides, polypeptides and/or proteins may be separated and purified prior to combination with a hydroxyl-terminated component herein. Techniques of separation and purification are within the purview of those skilled in the art and include, for example, homogenization, filtration, centrifugation, heat denaturation, ammonium sulfate precipitation, desalting, pH precipitation, ion exchange chromatography, hydrophobic interaction chromatography, affinity chromatography, combinations thereof, and the like.

In embodiments, suitable bioactive peptides for inclusion in the compositions of the present disclosure include any peptide that provides a desired pharmacological or biological activity. Examples of suitable bioactive peptides include, but are not limited to, coagulation modulators, cytokines, endorphins, kinins, hormones, extracellular matrix peptides (EMP), peptides containing an RGD (Arg-Gly-Asp) motif, antimicrobial peptides, angiogenic peptides, antitumoral peptides, cell adhesion inhibitors, cell activation inhibitors, and combinations thereof. As would be appreciated by one skilled in the art, a bioactive peptide may fall into more than one of the above categories.

Suitable coagulation modulators include, for example, $\alpha_1$-antitrypsin, $\alpha_2$-macroglobulin, antithrombin III, factor I (fibrinogen), factor II (prothrombin), factor III (tissue prothrombin), factor V (proaccelerin), factor VII (proconvertin), factor VIII (antihemophilic globulin or AHG), factor IX (Christmas factor, plasma thromboplastin component or PTC), factor X (Stuart-Power factor), factor XI (plasma thromboplastin antecedent or PTA), factor XII (Hageman factor), heparin cofactor II, kallikrein, plasmin, plasminogen, prekallikrein, protein C, protein S, thrombomodulin, and combinations thereof. Both "active" and "inactive" versions of these proteins may be utilized.

Suitable cytokines include, for example, colony stimulating factor 4, heparin binding neurotrophic factor (HBNF), interferon-$\alpha$, interferon $\alpha$-2$\alpha$, interferon $\alpha$-2b, interferon $\alpha$-n3, interferon-$\beta$, interferon-$\gamma$, interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, tumor necrosis factor, tumor necrosis factor-$\alpha$, granuloycte colony-stimulating factor (G-CSF), granulocyte-macrophage colony-stimulating factor (GM-CSF), macrophage colony-stimulating factor, midkine (MD), thymopoietin, and combinations thereof.

Suitable endorphins include, but are not limited to, dermorphin, dynorphin, $\alpha$-endorphin, $\beta$-endorphin, $\gamma$-endorphin, $\Sigma$-endorphin, [Leu$^5$]enkephalin, [Met$^5$]enkephalin, substance P, and combinations thereof.

In embodiments, kinins which may be utilized include bradykinin, bradykinin potentiator B, bradykinin potentiator C, kallidin, and combinations thereof.

Suitable peptide hormones include activin, amylin, angiotensin, atrial natriuretic peptide (ANP), calcitonin (derived from chicken, eel, human, pig, rat, salmon, and the like), calcitonin gene-related peptide, calcitonin N-terminal flanking peptide, cholecystokinin (CCK), ciliary neurotrophic factor (CNTF), corticotropin (adrenocorticotropin hormone, ACTH), corticotropin-releasing factor (CRF or CRH), epideinial growth factor (EGF), follicle-stimulating hormone (FSH), gastrin, gastrin inhibitory peptide (GIP), gastrin-releasing peptide, ghrelin, glucogon, gonadotropin-releasing factor (GnRF or GNRH), growth hormone releasing factor (GRF, GRH), human chorionic gonadotropin (hCG), inhibin A, inhibin B, insulin (derived from beef, human, pig, and the like), leptin, lipotropin (LPH), luteinizing hormone (LH), luteinizing hormone-releasing hormone (LHRH), LHRH analogs, $\alpha$-melanocyte-stimulating hormone, $\beta$-melanocyte-stimulating hormone, $\gamma$-melanocyte-stimulating hormone, melatonin, motilin, oxytocin (pitocin), pancreatic polypeptide, parathyroid hormone (PTH), placental lactogen, prolactin (PRL), prolactin-release inhibiting factor (PIF), prolactin-releasing factor (PRF), secretin, somatotropin (growth hormone, GH), somatostatin (SIF, growth hormone-release inhibiting factor, GIF), thyrotropin (thyroid-stimulating hormone, TSH), thyrotropin-releasing factor (TRH or TRF), thyroxine, triiodothyronine, vasoactive intestinal peptide (VIP), vasopressin (antidiuretic hormone, ADH), and combinations thereof.

In embodiments, analogues of LHRH which may be utilized include buserelin, deslorelin, fertirelin, goserelin, histrelin, leuprolide (leuprorelin), lutrelin, nafarelin, tryptorelin, and combinations thereof.

Other peptides that provide a desired pharmacological or biological activity can also be incorporated into the compositions of the present disclosure as bioactive peptides. Examples of such peptides include abarelix, adenosine deaminase, anakinra, ancestim, alteplase, alglucerase, asparaginase, bivalirudin, bleomycin, bombesin, desmopressin acetate, des-Q14-ghrelin, domase-α, enterostatin, erythropoietin, exendin-4, fibroblast growth factor-2, filgrastim, β-glucocerebrosidase, gonadorelin, hyaluronidase, IgG antibody fragments, insulinotropin, lactoferricin, lepirudin, magainin I, magainin II, nerve growth factor, neurofilament peptides, pentigetide, polylysine, telomerase inhibitors, thrombopoietin, thymosin α-1, thymidin kinase, tissue plasminogen activator, tryptophan hydroxylase, urokinase, urotensin II, and combinations thereof.

Yet other suitable peptides and proteins which can be incorporated into compositions of the present disclosure as bioactive peptides include tissue-healing enhancing agents, also known as tissue regenerative agents, including collagen; glycosaminoglycans such as hyaluronic acid, heparin, heparin sulfate, chondroitin sulfate, and the like; proteoglycans including versican, biglycan, and the like; substrate adhesion molecules such as fibronectin, vitronectin, laminin and the like; polypeptide growth factors including platelet-derived growth factor, fibroblast growth factor, transforming growth factor, insulin-like growth factor, and the like; and other peptides such as osteopontin and thrombospondin, as well as combinations of any of the foregoing. In embodiments, the tissue-healing enhancing agents may possess the tripeptide sequence RGD (arginine-glycine-aspartic acid), a sequence generally associated with adhesive proteins and necessary for interaction with cell surface receptors.

Methods for forming the compositions of the present disclosure are within the purview of those skilled in the art. In embodiments the hydroxyl-terminated component and the bioactive peptide may be combined utilizing a blocking method, whereby the hydroxyl-terminated component reacts with and links to the bioactive peptide. Another end of the hydroxyl-terminated component then reacts with another bioactive peptide forming a block

A-B-A wherein A is the bioactive peptide and B is the hydroxyl-terminated component. Additional bioactive peptide and hydroxyl-terminated component may then be added thereby forming a polymeric chain possessing the bioactive peptide conjugated thereto of the formula

ABABABABABA . . .

or

AAAAABBBBB where A and B are as defined above. Thus, in embodiments, the biodegradable composition of the present disclosure may have a formula $(AB)_n$ where A and B are as defined above and n is a number from about 5 to about 500, in embodiments from about 50 to about 250.

In other embodiments, the peptide may be functionalized to include at least one hydroxy end group. This hydroxy functional peptide, in turn, may then be combined with a cyclic monomer. Suitable cyclic monomers include, for example, cyclic esters such as lactones, and cyclic carbonates. Suitable cyclic esters may include those having small rings, in embodiments 5-member rings, in other embodiments 6-member rings, and in other embodiments 7-member rings. In some embodiments, suitable cyclic esters may possess a heteroatom, such as oxygen, adjacent to the α-carbon. Suitable cyclic esters include glycolide, L(−)-lactide, D(+)-lactide, meso-lactide, p-dioxanone, 1,4-dioxan-2one, 1,5-dioxepan-2-one, epsilon-caprolactone, delta-valerolactone, gamma-butyrolactone, beta-propiolactone, combinations thereof, and the like.

Suitable cyclic carbonates include, for example, ethylene carbonate, trimethylene carbonate, dimethyl trimethylene carbonate, 3-ethyl-3-hydroxymethyl trimethylene carbonate, propylene carbonate, trimethylolpropane monocarbonate, 4,6 dimethyl-1,3-propylene carbonate, 2,2-dimethyl trimethylene carbonate, 1,3-dioxepan-2-one, and combinations thereof.

In embodiments, the combination of a hydroxy functional peptide and cyclic monomer may produce a copolymer. Copolymers of the present disclosure may be formed by combining the cyclic monomer and hydroxy functional peptide utilizing any method or process within the purview of those skilled in the art. In embodiments, copolymers of the present disclosure may be obtained by subjecting the cyclic monomers to a ring-opening polymerization reaction initiated by the hydroxy functional peptide. The result of such a polymerization reaction may include both an ester and/or carbonate derivatives from the cyclic monomer(s), and a peptide derivative from the hydroxy functional peptide. Thus, in some embodiments, compositions of the present disclosure may be of the following formula:

$$B\text{-}O\text{-}A \quad (I)$$

wherein B is a derivative obtained from the cyclic monomer, in embodiments an ester or carbonate, and A is the peptide derivative obtained from the hydroxy functional peptide.

In other embodiments, where the hydroxy functional peptide contains two hydroxyl functional groups, i.e., each end of the peptide possesses a hydroxy group, the resulting composition of the present disclosure may be of the formula:

$$B\text{-}O\text{-}A\text{-}O\text{-}B \quad (II)$$

wherein B and A are as defined above.

In yet other embodiments, peptides of the present disclosure may be combined with a polyalkylene oxide (PAO). Suitable polyalkylene oxides which may be combined with a peptide include, but are not limited to, polyethylene glycols ("PEG"), polypropylene glycols ("PPG"), polyethylene oxides ("PEO"), polypropylene oxides ("PPO"), polyethylene glycols with lactide linkages, polyethylene glycols with caprolactone or polycaprolactone linkages, polypropylene glycol-co-polyethylene oxide block or random copolymers, polyethylene oxide/polypropylene oxide copolymers, sometimes referred to herein as PEO/PPO copolymers or poloxamers, including triblock PEO/PPO copolymers commercially available as PLURONICS® from BASF Corporation (Mt. Olive, N.J.), combinations thereof, and the like.

In embodiments, a peptide combined with such a polyalkylene oxide (PAO) may be referred to herein, for example, as "pegylated." The PAO group may be of any convenient molecular weight and may be linear or branched. The average molecular weight of the PAO may be from about 2 kiloDalton ("kDa") to about 100 kDa, in embodiments from about 5 kDa to about 50 kDa, in other embodiments from about 5 kDa to about 10 kDa. In embodiments, the PAO groups may be attached to the peptides via acylation or reductive alkylation through a reactive group on the PAO moiety (e.g., an aldehyde, amino, thiol, or ester group) to a free amino on the peptide or an additional functional group added to a synthetic peptide. In embodiments the peptides may be "preactivated" by the addition of an appropriate functional group at a specific site.

In embodiments, pegylation of peptides may include combining, through forming a conjugate linkage in solution, a peptide and a PAO moiety, each bearing a functionality that is mutually reactive toward the other. The resulting pegylated peptide may thus be of the following formula:

A-C-OH    (III)

wherein A is a peptide as described above and C is a PAO. The above pegylated peptide may then be reacted with a cyclic monomer described above, thus forming a composition of the present disclosure of the following formula:

A-C-O-B    (IV)

wherein A, B, and C are as defined above.

In some cases it may be desirable to allow the reaction of the peptide and hydroxyl-terminated component, in embodiments a ring-opening polymerization as described above, to occur under a vacuum, e.g., at a pressure less than about 1 Torr.

In some embodiments it may be desirable to heat the peptide and hydroxyl-terminated component, in embodiments a cyclic monomer, to a suitable temperature of from about 170° C. to about 185° C., in embodiments from about 175° C. to about 180° C., in some cases to a temperature of about 178° C. The components may be allowed to polymerize for a suitable period of time of from about 4 hours to about 6 hours, in embodiments from about 4.25 hours to about 4.75 hours.

After this time, the resulting molten copolymer may be obtained. While not necessary, in some embodiments the composition of the present disclosure may be subjected to a further heat treatment by heating to a temperature of from about 100° C. to about 120° C., in embodiments from about 107° C. to about 113° C., for a period of time from about 25 hours to about 35 hours, in embodiments from about 28 hours to about 32 hours. In some cases it may be desirable for this second heat treatment to occur under a vacuum, in embodiments at a pressure less than about 1 Torr.

The derivative obtained from the cyclic monomer, in embodiments an ester or carbonate, can be present in an amount up to about 95% by total weight of the composition of the present disclosure, in embodiments from about 5% to about 95% by total weight of the composition of the present disclosure, in other embodiments from about 20% to about 60% by total weight of the composition of the present disclosure. Thus, the peptide derivative obtained from the bioactive peptide, in embodiments a hydroxyl functional peptide, may be present in an amount up to about 95% by total weight of the composition of the present disclosure, in embodiments from about 5% to about 95% by total weight of the composition of the present disclosure, in other embodiments from about 40% to about 80% by total weight of the composition of the present disclosure.

In addition, the compositions of the present disclosure may be combined with other biocompatible polymers, so long as they do not interfere undesirably with the biodegradable characteristics of the composition. Blends of the copolymers of the present disclosure with such other polymers may offer even greater flexibility in designing the precise release profile desired for targeted drug delivery or the precise rate of biodegradability desired for structural implants. Examples of such additional biocompatible polymers include other polycarbonates; polyesters; polyorthoesters; polyamides; polyurethanes; poly(iminocarbonates); polyanhydrides; and combinations thereof.

Upon application in situ, the hydroxyl-terminated component of the composition of the present disclosure may degrade, in embodiments by hydrolysis, thereby releasing the bioactive peptide in situ. Thus, compositions of the present disclosure may, in embodiments, be referred to herein as "biodegradable compositions."

In embodiments, the hydroxyl-terminated component and the bioactive peptide can be individually formed and then reacted to form the desired composition of the present disclosure. In embodiments, the composition of the present disclosure can be prepared using conventional techniques. For example, monomers can be dried, mixed in a reaction vessel with an initiator (either a single or multi-functional initiator) and a suitable polymerization catalyst, and heated at temperatures of from about 160° C. to about 200° C., for a period of time of from about 5 hours to about 10 hours. Then, the bioactive peptide may be added directly to the reactor where it reacts with the hydroxyl-terminated component to thereby form an AB section of the composition of the present disclosure. Additional hydroxyl-terminated components may then be added as described above, and optionally additional peptides, thereby forming an ABA composition.

Once formed, it may be desirable in some embodiments to end cap the resulting polymeric chain.

For example, isocyanate endcapping can be achieved by reacting the resulting polymer with a diisocyanate. Suitable isocyanates for endcapping the polyester or poly(ether-ester) block include aromatic, aliphatic and alicyclic isocyanates. Examples include, but are not limited to, aromatic diisocyanates such as 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, 4,4'-oxybis(phenylisocyanate) or tetramethylxylylene diisocyanate; aliphatic diisocyanates such as tetramethylene diisocyanate, hexamethylene diisocyanate, dimethyl diisocyanate, lysine diisocyanate, 2-methylpentane-1,5-diisocyanate, 3-methylpentane-1,5-diisocyanate or 2,2,4-trimethylhexamethylene diisocyanate; and alicyclic diisocyanates such as isophorone diisocyanate, cyclohexane diisocyanate, hydrogenated xylylene diisocyanate, hydrogenated diphenylmethane diisocyanate, hydrogenated trimethylxylylene diisocyanate, 2,4,6-trimethyl 1,3-phenylene diisocyanate or commercially available DESMODURS® from Bayer Material Science.

Methods for endcapping the polyester or poly(ether-ester) block with a diisocyanate are within the purview of those skilled in the art. The conditions under which the polymer is reacted with the diisocyanate may vary widely depending on the specific polymer being end capped, the specific diisocyanate being employed, and the desired degree of end capping to be achieved. In some embodiments, the polyester or poly(ether-ester) block may be combined with a suitable diisocyanate, in embodiments a toluene diisocyanate, and heated to a suitable temperature from about 55° C. to about 75° C., in embodiments from about 60° C. to about 70° C., in embodiments about 65° C. The amount of diisocyanate employed can range from abodt 2 to about 8 moles of diisocyanate per mole of polymer. Suitable reaction times and temperatures range from about 15 minutes to about 72 hours or more at temperatures ranging from about 0° C. to about 250° C. In some embodiments the resulting diisocyanate-functional composition may then be obtained by hot extraction with petroleum ether.

Once endcapped with isocyanate, the endcapped polymers may be cross-linked. Cross-linking may be performed by exposing the endcapped polymer to water in the presence of a catalyst, such as a tertiary amine catalyst.

The exact reaction conditions for achieving cross-linking will vary depending on a number of factors such as the composition of the polymer, the degree of endcapping, the specific isocyanate used to end cap and the desired degree of cross-linking. Normally, the cross-linking reaction may be conducted at temperatures ranging from about 20° C. to about 40° C. for about five minutes to about 72 hours or more. The amount of water employed may be from about 0.05 moles to about 1 mole per mole of polymer. Other compositions could also be employed either together with or instead of water. Such compositions include diethylene glycol, polyethylene glycol and diamines, such as, for example, diethylamino propanediol. Suitable catalysts for use in the cross-linking reaction include 1,4diazobicyclo [2.2.2] octane, triethylamine, and diethylaminoethanol.

The amount of catalyst employed can range from about 0.5 grams to about 50 grams per kilogram of polymer being cross-linked.

When the composition is intended for implantation it is possible to effectuate cross-linking in situ using the water naturally present in a mammalian body or with added water.

The isocyanate endcapped polymers can also be cross-linked by the application of heat alone, or by exposing the polymer to diamine vapor. These cross-linking techniques are particularly useful when the polymers are to be used as an adhesive or sealant.

In an alternative embodiment, the isocyanate endcapped polymers described herein may be admixed with a filler prior to cross-linking. Any known filler may be used, including hydroxyapatite, tricalcium phosphate, bioglass or other bioceramics. Normally, from about 10 grams to about 400 grams of filler may be mixed with about 100 grams of polymer. Cross-linking of the polymer/filler mixture can be carried out using any of the above-described methods. The filled, cross-linked polymers may be useful, for example, as a molding composition. As another example, the filled endcapped polymer (with or without crosslinking) can be packed into a bone fusion implant (e.g., fusion cage, plug, hip joint prosthesis, etc.) as a bone-growth-inducing substance. The use of such packed implants is disclosed, for example, in U.S. Pat. No. 5,026,373 the entire disclosure of which is incorporated herein by this reference. The filled polymers are stable for several months when kept dry. These dry mixtures will cross-link upon exposure to water without dispersing in water.

Besides the isocyanates described above, in other embodiments free hydroxyl groups at the ends of the compositions of the present disclosure, in embodiments from the hydroxyl-terminated component, may be further functionalized with nucleophilic groups, electrophilic groups, combinations thereof, and the like.

In some embodiments it may be desirable to functionalize the free hydroxyl groups at the ends of the compositions of the present disclosure with electrophilic groups. Examples of suitable electrophilic groups include, but are not limited to, carbodiimidazole, sulfonyl chloride, chlorocarbonates, n-hydroxysuccinimidyl ester, succinimidyl ester, sulfasuccinimidyl esters, and combinations thereof. Methods for forming such groups on free hydroxy groups at the ends of compositions of the present disclosure are within the purview of those skilled in the art. For example, in some embodiments the free hydroxyl groups may be converted to carboxylic groups by reacting them with anhydrides such as succinic anhydride in the presence of tertiary amines such as pyridine or triethylamine or dimethylaminopyridine ("DMAP"). Other anhydrides which may be utilized include, but are not limited to, glutaric anhydride, phthalic anhydride, maleic anhydride, combinations thereof, and the like. The resultant terminal carboxyl groups may then be reacted with N-hydroxysuccinimide, optionally in the presence of dicyclohexylcarbodiimide ("DCC"), to produce N-hydroxysuccinimide ester groups, which are electrophilic, at the ends of the biocompatible component of the present disclosure.

Similarly, other free hydroxyl groups at the ends of the compositions of the present disclosure may be functionalized with nucleophilic groups. Suitable nucleophilic groups include, but are not limited to, amine, hydroxyl, carboxyl, thiol, and combinations thereof. These nucleophilic functional compositions may then be combined with the above electrophilic functional compositions to produce a macromer including the compositions of the present disclosure.

Combinations of electrophilic groups, nucleophilic groups, or both, may be utilized to functionalize free hydroxyl groups located at the ends of compositions of the present disclosure.

In embodiments, compositions of the present disclosure having electrophilic groups may react with may compositions of the present disclosure having nucleophilic groups. This may increase the rate of formation of compositions of the present disclosure. This may also facilitate the formation of macromers including the compositions of the present disclosure.

The resulting compositions of the present disclosure can be used for a number of different human and animal medical applications including, but not limited to, drug delivery devices, wound closure (including surgical incisions and other wounds), adhesives for medical devices (including implants), sealants, and embolic agents.

Where utilized as a drug delivery device, the hydroxyl-terminated component of the biodegradable composition of the present disclosure may degrade in vivo, thereby releasing the bioactive peptide described above whereupon the bioactive peptide may exert its effects in vivo. Similarly, an adhesive or sealant using the composition of the present disclosure, in addition to functioning as an adhesive or sealant, may also release a bioactive peptide as the hydroxyl-terminated component of the biodegradable composition degrades in vivo after fulfilling its function as an adhesive or sealant.

In embodiments, the biodegradable compositions of the present disclosure may be mixed with a polar solvent. Suitable polar solvents which may be utilized are within the purview of those skilled in the art and include, for example, water, alcohols such as ethanol, triethylene glycol, methoxypolyethylene glycols, dimethylformamide, dimethylacetamide, gamma-butyrolactone, N-methylpyrrolidone, ketones such as methylethyl ketone, cyclohexanone, ethers such as diethyl ether, and mixtures of these and other polar solvents.

The polar solvent may be mixed with the biodegradable composition of the present disclosure at a ratio of from about 1:0.25 to about 1:10 w/w, in embodiments at a ratio of from about 1:1 to about 1:4 w/w.

The mixture of the biodegradable composition of the present disclosure and polar solvent as described herein may result in an emulsion or a diluted solution. The viscosity of the resulting emulsion,or solution may be below about 400 cP, in embodiments below about 200 cP. In some embodiments, the viscosity of the resulting emulsion or solution may be from about 5 cP to about 400 cP, in other embodiments from about 25 cP to about 300 cP, in still other embodiments from about 50 cP to about 150 cP. The decreased viscosity improves the spraying of the emulsion or solution without sacrificing the adherence and physico-mechanical properties of the composition as an adhesive, sealant or drug delivery system.

The concentrations of the hydroxyl-terminated component and the bioactive peptide in the composition of the present disclosure will vary depending upon a number of factors, including the types and molecular weights of the particular components used and the desired end use application, i.e., to form a composition of the present disclosure for use as a drug delivery device, an adhesive or sealant. Compositions of the present disclosure may take various forms including, but not limited to, particles including microspheres or nanospheres, or insoluble viscous fluids. Where the composition is intended for delivery of a drug or protein, the amounts of the components making up the compositions of the present disclosure can be adjusted to promote the initial retention of the drug or polymer in the biodegradable composition and its subsequent release. Methods and means for making such adjustments will be readily apparent to those skilled in the art.

Methods for administering bioactive peptides to animals utilizing the compositions of the present disclosure are also contemplated. For administration to an animal, including a mammal, the composition of the present disclosure may be introduced to an animal using any method within the purview of those skilled in the art. Such methods include, but are not limited to, parenteral, transdermal, subcutaneous, transmucosal, intravenous, ocular, vaginal, urethral, buccal, pulmonary, transurethral, rectal, intrarespiratory, nasal, oral, aural, sublingual, conjunctival, and the like. For example, in embodiments, injection and/or implantation of a composition of the present disclosure may occur subcutaneously, intramuscularly, intraperitoneally, intradermally, intravenously, intraarterially, or intrathecally. In other embodiments, administration may occur by application to dermal or mucosal membranes. The route of administration may be chosen to optimize delivery of the bioactive peptide to the desired site in the animal. Once delivered, the hydroxyl-terminated component may degrade in vivo, thereby releasing the bioactive peptide to the desired locus within the animal's body.

In embodiments, the composition of the present disclosure may be combined with a pharmaceutically acceptable carrier for administration to an animal. Any carrier within the purview of those skilled in the art may be utilized to administer a composition of the present disclosure. For example, formulations suitable for injection include those found in Remington's Pharmaceutical Sciences, Mack Publishing Company, Philadelphia, Pa., 17th ed. (1985). Formulations utilized to administer compositions of the present disclosure should be sterile and non-pyrogenic, and generally include a pharmaceutically effective carrier, such as saline, buffered (e.g., phosphate buffered) saline, Hank's solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like.

In embodiments, it may be useful to endcap the composition of the present disclosure with an isocyanate as described above prior to administration. Endcapping may be especially useful where the composition of the present disclosure is intended to be used as an adhesive and/or sealant.

Where the biodegradable compositions of the present disclosure are used to produce adhesives or sealants, additional optional ingredients including medicinal agents may also be added to the biodegradable compositions of the present disclosure. A phospholipid surfactant, or phospholipid polymers such as 2-methacryloyloxyethyl phosphorylcholine (MPC), which provides antibacterial stabilizing properties and helps disperse other materials in the biodegradable composition, may also be added. Additional medicinal agents which may be included with a composition of the present disclosure include antimicrobial agents, colorants, preservatives, or medicinal agents such as, for example, protein and peptide preparations, antipyretic, antiphlogistic and analgesic agents, anti-inflammatory agents, vasodilators, antihypertensive and antiarrhythmic agents, hypotensive agents, antitussive agents, antineoplastics, local anesthetics, hormone preparations, antiasthmatic and antiallergic agents, antihistaminics, anticoagulants, antispasmodics, cerebral circulation and metabolism improvers, antidepressant and antianxiety agents, vitamin D preparations, hypoglycemic agents, antiulcer agents, hypnotics, antibiotics, antifungal agents, sedative agents, bronchodilator agents, antiviral agents, polymer drugs, and dysuric agents. Methods for combining these medicinal agents with compositions of the present disclosure are within the purview of those skilled in the art and include, but are not limited to, mixing, blending, and the like.

Imaging agents such as iodine or barium sulfate, or fluorine, can also be combined with the compositions of the present disclosure to allow visualization of the surgical area through the use of imaging equipment, including X-ray, MRI, and CAT scan.

Additionally, an enzyme may be added to the composition of the present disclosure to increase its rate of degradation. Suitable enzymes include, for example, peptide hydrolases such as elastase, cathepsin G, cathepsin E, cathepsin B, cathepsin H, cathepsin L, trypsin, pepsin, chymotrypsin, γ-glutamyltransferase (γ-GTP) and the like; sugar chain hydrolases such as phosphorylase, neuraminidase, dextranase, amylase, lysozyme, oligosaccharase and the like; oligonucleotide hydrolases such as alkaline phosphatase, endoribonuclease, endodeoxyribonuclease and the like. In some embodiments, where an enzyme is added, the enzyme may be included in a liposome or microsphere to control the rate of its release, thereby controlling the rate of degradation of the biodegradable composition of the present disclosure. Methods for incorporating enzymes into liposomes and/or microspheres are within the purview of those skilled in the art.

In embodiments, combinations of any one or more of the foregoing medicinal agents may be combined with the compositions of the present disclosure.

In embodiments, the biodegradable compositions may be used to bind tissue together either as a replacement of, or as a supplement to, sutures, staples, tapes and/or bandages. Use of the disclosed compositions as an adhesive can eliminate or substantially reduce the number of sutures normally required during current practices, and eliminate the subsequent need for removal of staples and certain types of sutures and thus can be particularly useful for use with delicate tissues where sutures, clamps or other conventional tissue closure mechanisms may cause further tissue damage.

Additional applications include sealing tissues to prevent or control blood, or other fluid leaks, at suture or staple lines. In another embodiment, the biodegradable composition can be used to attach skin grafts and position tissue flaps during reconstructive surgery. In still another embodiment, the adhesive can be used to close tissue flaps in periodontal surgery.

To effectuate the joining of two tissue edges, the two edges are approximated, and the composition of the present disclosure is applied, in embodiments, by spraying. The biodegradable composition, in embodiments endcapped with, for example, an isocyanate, may then be combined with water or moisture in situ whereby it will crosslink rapidly, generally taking less than one minute. The composition of the present disclosure can be used as an adhesive to close a wound, including a surgical incision. In such a case, the composition of the present disclosure can be applied to the wound and allowed to set, thereby closing the wound.

While certain distinctions may be drawn between the usage of the terms "flesh" and "tissue" within the scientific community, the terms are used interchangeably herein as referring to a general substrate upon which those skilled in the art would understand the present composition to be utilized within the medical field for the treatment of patients. As used herein, "tissue" may include, but is not limited to, skin, bone, neuron, axon, cartilage, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic or ascite tissue.

In another embodiment, the present disclosure is directed to a method for using the biodegradable composition of the present disclosure to adhere a medical device to tissue, rather than secure two edges of tissue. In some embodiments, depending on the composition of the medical device, a coating may be required on the medical device. In some cases such a coating can include the biodegradable composition of the present disclosure. In some aspects, the medical device includes an implant. Other medical devices include, but are not limited to, pacemakers, stents, shunts, catheters, tissue scaffolds, and the like. Generally, for adhering a device to the surface of animal tissue, the composition of the present disclosure can be applied to the device, the tissue surface or both. The device, biodegradable composition and tissue surface are then brought into contact with each other and the composition is allowed to set, thereby adhering the device and surface to each other.

The compositions of the present disclosure can also be used to prevent post surgical adhesions. In such an application, the biodegradable composition is applied and cured as a layer on surfaces of internal tissues in order to prevent the formation of adhesions at a surgical site during the healing process.

In addition to the formation of adhesion barriers, in embodiments the biodegradable compositions may be utilized to form implants such as gaskets, buttresses, or pledgets for implantation.

When used as a sealant, the composition of the present disclosure can be used in surgery to prevent or inhibit bleeding or fluid leakage both during and after a surgical procedure. It can also be applied to prevent air leaks associated with pulmonary surgery. The sealant may be applied directly to the desired area in at least an amount necessary to seal off any defect in the tissue and seal off any fluid or air movement.

The present biodegradable composition has a number of advantageous properties. The resulting biodegradable compositions of the present disclosure are safe and biocompatible, possess enhanced adherence to tissue, are biodegradable, have hemostatic potential, have low cost, and are easy to prepare and use. By incorporating hydroxyl-terminated components in the biodegradable compositions of the present disclosure, the drug delivery, adhesive or sealant composition of the present disclosure prepared from the biodegradable compositions described herein may be more susceptible to non-specific hydrolysis, faster degradation, and faster mass loss, without any negative effects to the mechanical performance of the drug delivery device, adhesive or sealant upon initial application in situ. The release of bioactive peptides in situ may be utilized for numerous beneficial effects, including wound healing and the like.

Various modifications and variations of the embodiments described herein will be apparent to those skilled in the art from the foregoing detailed description. Such modifications and variations are intended to come within the scope of the following claims.

What is claimed is:

1. A biodegradable composition comprising:
   at least one hydroxyl-terminated component; and
   at least one bioactive peptide,
   wherein the biodegradable composition comprises a linear chain of the formula $(AB)_n$, wherein A is the at least one bioactive peptide, B is the at least one hydroxyl-terminated component, and n is a number from about 5 to about 500, and degradation of the at least one hydroxyl-terminated component releases the bioactive peptide in vivo,
   and wherein the biodegradable composition further comprises at least one medicinal agent selected from the group consisting of antimicrobial agents, colorants, preservatives, protein preparations, peptide preparations, antipyretic agents, antiphlogistic agents, analgesic agents, anti-inflammatory agents, vasodilators, antihypertensive agents, antiarrhythmic agents, hypotensive agents, antitussive agents, antineoplastics, local anesthetics, hormone preparations, antiasthmatic agents, antiallergic agents, antihistaminics, anticoagulants, antispasmodics, cerebral circulation improvers, metabolism improvers, antidepressant agents, antianxiety agents, vitamin D preparations, hypoglycemic agents, antiulcer agents, hypnotics, antibiotics, antifungal agents, sedative agents, bronchodilator agents, antiviral agents, dysuric agents, and combinations thereof.

2. The biodegradable composition of claim 1, wherein the at least one hydroxyl-terminated component is selected from the group consisting of polyesters, and poly(ether-esters).

3. The biodegradable composition of claim 1, wherein the at least one hydroxyl-terminated component comprises a polyester selected from the group consisting of trimethylene carbonate, ε-caprolactone, p-dioxanone, glycolide, lactide, 1,5-dioxepan-2-one, polybutylene adipate, polyethylene adipate, polyethylene terephthalate, polymers thereof, and copolymers thereof.

4. The biodegradable composition of claim 1, wherein the at least one hydroxyl-terminated component comprises a poly(ether-ester) block selected from the group consisting of polyethylene glycol-polycaprolactone, polyethylene glycol-polylactide, polyethylene glycol-polyglycolide, polyethylene glycol-lactide-glycolide, polyethylene glycol-lactide-caprolactone, polyethylene glycol-trimethylene carbonate, polyethylene glycol-trimethylene carbonate-lactide, polyethylene glycol-trimethylene carbonate-glycolide, polyethylene glycol-trimethylene carbonate-caprolactone, and polyethylene glycol-glycolide-caprolactone.

5. The biodegradable composition of claim 1, wherein the at least one bioactive peptide is selected from the group consisting of coagulation modulators, cytokines, endorphins, kinins, hormones, extracellular matrix peptides, peptides containing an RGD motif, antimicrobial peptides, angiogenic peptides, anti-tumoral peptides, cell adhesion inhibitors, cell activation inhibitors, and combinations thereof.

6. The biodegradable composition of claim 1, wherein the at least one bioactive peptide comprises a coagulation modulator selected from the group consisting of $\alpha_1$-antitrypsin, $\alpha_2$-macroglobulin, antithrombin III, fibrinogen, prothrombin, tissue prothrombin, proaccelerin, proconvertin, antihemophilic globulin, plasma thromboplastin component, Stuart-Power factor, plasma thromboplastin antecedent, Hageman factor, heparin cofactor II, kallikrein, plasmin, plasminogen, prekallikrein, protein C, protein S, thrombomodulin, and combinations thereof.

7. The biodegradable composition of claim 1, wherein the at least one bioactive peptide comprises a cytokine selected from the group consisting of colony stimulating factor 4, heparin binding neurotrophic factor, interferon-α, interferon α-2α, interferon α-2b, interferon α-n3, interferon-β, interferon-γ, interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, tumor necrosis factor, tumor necrosis factor-α, granuloycte colony-stimulating factor, granulocyte-macrophage colony-stimulating factor, macrophage colony-stimulating factor, midkine, thymopoietin, and combinations thereof.

8. The biodegradable composition of claim 1, wherein the at least one bioactive peptide comprises an endorphin selected from the group consisting of dermorphin, dynorphin, α-endorphin, β-endorphin, γ-endorphin, Σ-endorphin, [Leu$^5$] enkephalin, [Met$^5$]enkephalin, substance P, and combinations thereof.

9. The biodegradable composition of claim 1, wherein the at least one bioactive peptide comprises a kinin selected from the group consisting of bradykinin, bradykinin potentiator B, bradykinin potentiator C, kallidin, and combinations thereof.

10. The biodegradable composition of claim 1, wherein the at least one bioactive peptide comprises a peptide selected from the group consisting of activin, amylin, angiotensin, atrial natriuretic peptide, calcitonin, calcitonin gene-related peptide, calcitonin N-terminal flanking peptide, cholecystokinin, ciliary neurotrophic factor, adrenocorticotropin hormone, corticotropin-releasing factor, epidermal growth factor, follicle-stimulating hormone, gastrin, gastrin inhibitory peptide, gastrin-releasing peptide, ghrelin, glucogon, gonadotropin-releasing factor, growth hormone releasing factor, human chorionic gonadotropin, inhibin A, inhibin B, insulin, leptin, lipotropin, luteinizing hormone, luteinizing hormone-releasing hormone, buserelin, deslorelin, fertirelin, goserelin, histrelin, leuprolide, lutrelin, nafarelin, tryptorelin, a-melanocyte-stimulating hormone, β-melanocyte-stimulating hormone, γ-melanocyte-stimulating hormone, melatonin, motilin, oxytocin, pancreatic polypeptide, parathyroid hormone, placental lactogen, prolactin, prolactin-release inhibiting factor, prolactin-releasing factor, secretin, somatotropin, somatostatin, thyroid-stimulating hormone, thyrotropin-releasing factor, thyroxine, triiodothyronine, vasoactive intestinal peptide, vasopressin and combinations thereof.

11. The biodegradable composition of claim 1, wherein the at least one bioactive peptide is selected from the group consisting of abarelix, adenosine deaminase, anakinra, ancestim, alteplase, alglucerase, asparaginase, bivalirudin, bleomycin, bombesin, desmopressin acetate, des-Q14-ghrelin, domase-α, enterostatin, erythropoietin, exendin-4, fibroblast growth factor-2, filgrastim, β-glucocerebrosidase, gonadorelin, hyaluronidase, IgG antibody fragments, insulinotropin, lactoferricin, lepirudin, magainin I, magainin II, nerve growth factor, neurofilament peptides, pentigetide, polylysine, telomerase inhibitors, thrombopoietin, thymosin α-1, thymidin kinase, tissue plasminogen activator, tryptophan hydroxylase, urokinase, urotensin II, and combinations thereof.

12. The biodegradable composition of claim 1, wherein the at least one bioactive peptide comprises a tissue-healing enhancing agent selected from the group consisting of glycosaminoglycans, proteoglycans, substrate adhesion molecules, polypeptide growth factors and combinations thereof.

13. A drug delivery device comprising the biodegradable composition of claim 1.

14. A method for delivering a bioactive peptide to an animal comprising administering the biodegradable composition of claim 1 to the animal.

15. A pharmaceutical composition comprising the biodegradable composition of claim 1 optionally in combination with a pharmaceutically acceptable carrier.

16. A surgical adhesive comprising the biodegradable composition of claim 1, optionally endcapped with a component selected from the group consisting of isocyanates, amines, hydroxyls, carboxyls, thiols, carbodiimidazoles, sulfonyl chlorides, chlorocarbonates, n-hydroxysuccinimidyl esters, succinimidyl esters, sulfasuccinimidyl esters, and combinations thereof.

17. A surgical sealant comprising the biodegradable composition of claim 1, optionally endcapped with an isocyanate.

18. A method comprising:
polymerizing at least one cyclic monomer in the presence of a hydroxy functional peptide to form a copolymer; and
recovering the resulting copolymer.

19. The method of claim 18, wherein the at least one cyclic monomer is selected from the group consisting of cyclic esters and cyclic carbonates.

20. The method of claim 18, wherein the at least one cyclic monomer comprises a cyclic ester selected from the group consisting of glycolide, L(−)-lactide, D(+)-lactide, meso-lactide, p-dioxanone, 1,4-dioxan-2-one, 1,5-dioxepan-2-one, epsilon-caprolactone, delta-valerolactone, gamma-butyrolactone, beta-propiolactone, and combinations thereof.

21. The method of claim 18, wherein at least one cyclic monomer comprises a cyclic carbonate selected from the group consisting of ethylene carbonate, trimethylene carbonate, dimethyl trimethylene carbonate, 3-ethyl-3-hydroxymethyl trimethylene carbonate, propylene carbonate, trimethylolpropane monocarbonate, 4,6 dimethyl-1,3-propylene carbonate, 2,2-dimethyl trimethylene carbonate, and 1,3-dioxepan-2-one, and combinations thereof.

22. The method of claim 18, wherein polymerizing the at least one cyclic monomer in the presence of the hydroxy functional peptide comprises heating the cyclic monomer and hydroxy functional peptide to a temperature of from about 170° C. to about 185° C., for a period of time from about 4 hours to about 6 hours.

23. The method of claim 18, further comprising heating the copolymer to a temperature from about 100° C. to about 120° C., for a period of time ranging from about 25 hours to about 35 hours.

24. A copolymer produced by the method of claim 18.

* * * * *